(12) United States Patent
Noguchi et al.

(10) Patent No.: US 9,574,998 B2
(45) Date of Patent: Feb. 21, 2017

(54) LINE SEGMENT DETECTION APPARATUS, AND STORAGE MEDIUM STORING CONTROL PROGRAM

(71) Applicant: Graphtec Corporation, a corporation duly organized and existing under the laws of Japan, Kanagawa (JP)

(72) Inventors: Masatoshi Noguchi, Kanagawa (JP); Tamao Umezawa, Kanagawa (JP)

(73) Assignee: Graphtec Corporation, Kanagawa (JP)

( * ) Notice: Subject to any disclaimer, the term of this patent is extended or adjusted under 35 U.S.C. 154(b) by 135 days.

(21) Appl. No.: 14/521,837

(22) Filed: Oct. 23, 2014

(65) Prior Publication Data
US 2015/0116716 A1    Apr. 30, 2015

(30) Foreign Application Priority Data

Oct. 30, 2013   (JP) ................. 2013-225753

(51) Int. Cl.
*G01N 21/55* (2014.01)
*B26D 5/00* (2006.01)
(Continued)

(52) U.S. Cl.
CPC ............... *G01N 21/55* (2013.01); *B26D 5/005* (2013.01); *B26D 5/34* (2013.01); *B26F 1/3813* (2013.01); *G01N 2201/10* (2013.01)

(58) Field of Classification Search
CPC ............. B26F 1/00; Y10T 83/00; B26D 5/00; B26D 7/00; G01N 21/89; G01V 8/10; G06M 7/00; B41J 11/00; B23K 26/00
(Continued)

(56) References Cited

U.S. PATENT DOCUMENTS

| 5,313,886 A | 5/1994 | Muller |
| 6,201,256 B1 | 3/2001 | Kouchi et al. |

(Continued)

FOREIGN PATENT DOCUMENTS

| EP | 1655622 | 5/2006 |
| JP | H11-114886 | 4/1999 |

OTHER PUBLICATIONS

Extended European Search Report from Application No. 14190075.3, issued Mar. 17, 2015, Graphtec Corp., pp. 1-4.

Primary Examiner — Tarifur Chowdhury
Assistant Examiner — Isiaka Akanbi
(74) Attorney, Agent, or Firm — Meyertons, Hood, Kivlin, Kowert & Goetzel, P.C.; Eric B. Meyertons

(57) ABSTRACT

A line segment detection apparatus includes a head that supports a sensor configured to detect light reflected by a surface of a cutting target medium, a driving unit configured to move the head in two-dimensional directions relatively to the medium, and a processing unit configured to drive the driving unit and perform arithmetic processing on an output of the sensor. The processing unit includes a region detection unit configured to detect a region different in reflectance from surroundings based on a change of a signal output from the sensor when the sensor was moved in a first direction, and a determination unit configured to determine whether the region is a line segment, based on the change of the signal output from the sensor when the sensor passed a point in the region and was moved in a second direction perpendicular to the first direction.

6 Claims, 11 Drawing Sheets

(51) Int. Cl.
  *B26D 5/34* (2006.01)
  *B26F 1/38* (2006.01)
(58) Field of Classification Search
  USPC .................................................. 356/445–448
  See application file for complete search history.

(56) References Cited

U.S. PATENT DOCUMENTS

| | | | |
|---|---|---|---|
| 6,616,360 B2* | 9/2003 | Lehmkuhl | B41J 11/663 400/352 |
| 6,768,502 B2* | 7/2004 | Milton | B41J 25/304 347/197 |
| 2002/0144578 A1 | 10/2002 | Mikkelsen et al. | |
| 2007/0034061 A1* | 2/2007 | Workman | B26D 5/00 83/27 |
| 2009/0000444 A1* | 1/2009 | Johnson | B26D 7/2614 83/76.1 |
| 2010/0037738 A1* | 2/2010 | Kobayashi | B26D 5/02 83/13 |
| 2010/0319507 A1* | 12/2010 | Tse | B41J 11/663 83/56 |

* cited by examiner

Prior Art

F I G. 1 3
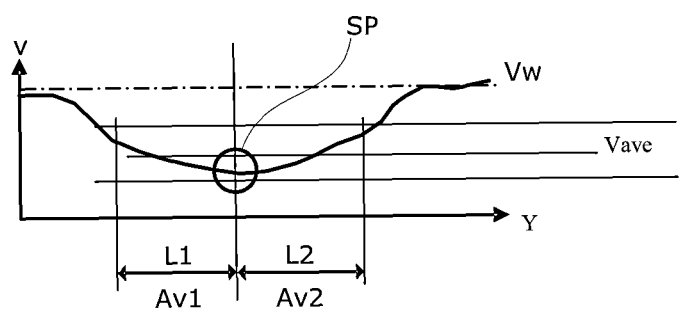
F I G. 1 4
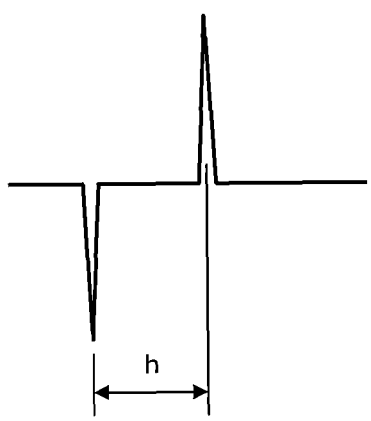

F I G. 1 5
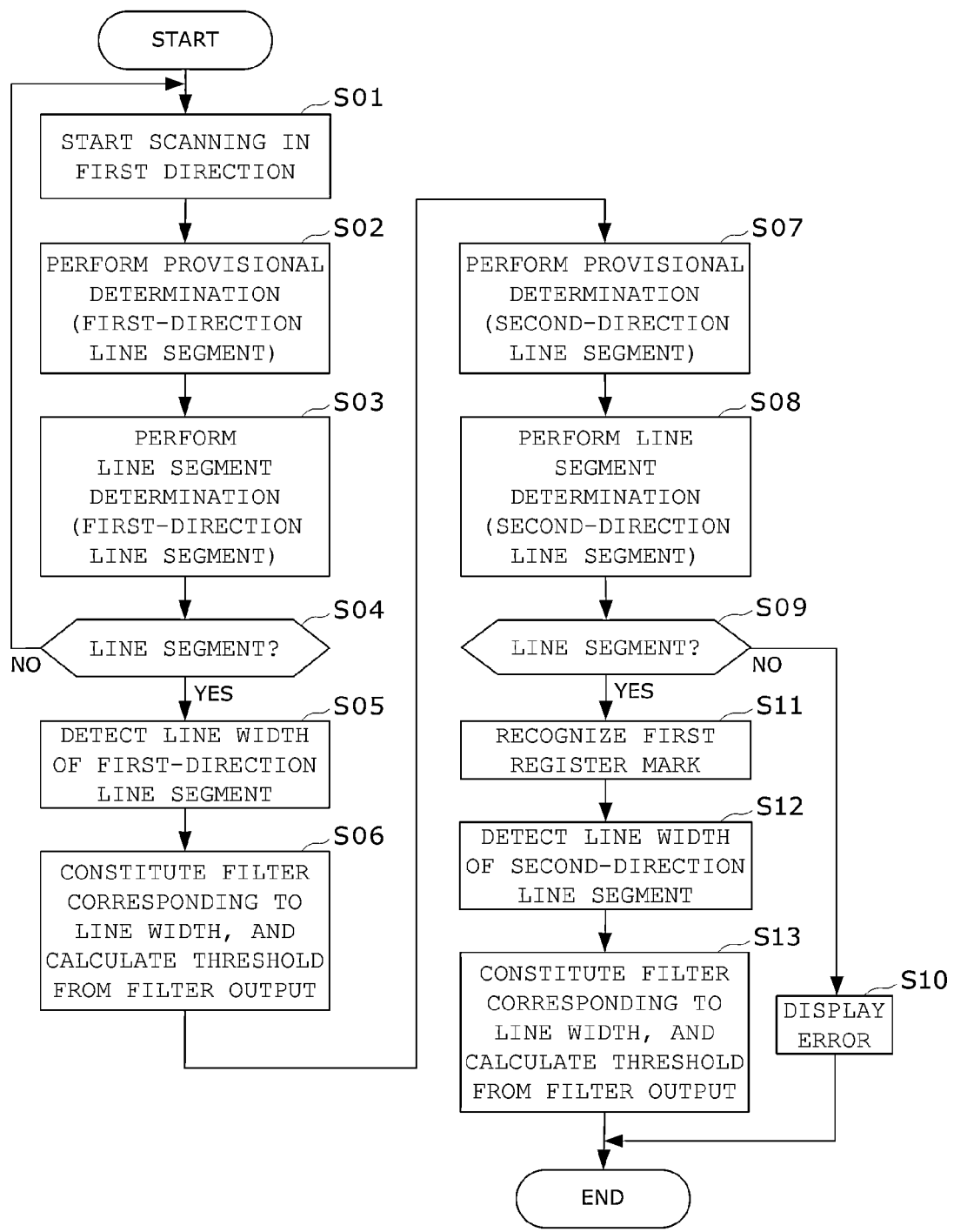

LINE SEGMENT DETECTION APPARATUS, AND STORAGE MEDIUM STORING CONTROL PROGRAM

PRIORITY CLAIM

This application claims priority to Japanese Patent Application No. 2013-225753 filed Oct. 30, 2013, which is incorporated herein by reference in its entirety.

BACKGROUND OF THE INVENTION

1. Field of the Invention

The present invention relates to a line segment detection apparatus and a storage medium storing a control program. More particularly, the present invention relates to a line segment detection apparatus applicable to a cutting plotter having a function of detecting the reference mark of a cutting target medium, and a storage medium storing a control program.

2. Description of the Relevant Art

These days, a so-called cutting target medium driving (grid roller) cutting plotter and a flatbed cutting plotter are known as a cutting plotter that cuts a cutting target medium into a desired shape.

The grid roller cutting plotter includes driving rollers (grid rollers) and driven rollers (pinch rollers) that clamp the two end portions of a cutting target medium. The grid roller cutting plotter moves a cutting target medium in the first direction (X-axis direction) by rotating the driving rollers clockwise and counterclockwise. The grid roller cutting plotter further includes a pen block provided to be movable in the second direction (Y-axis direction) perpendicular to the first direction. A cutting pen attached to the pen block is moved in the second direction (Y-axis direction) while being selectively pressed against or separated from a cutting target medium. In this manner, the grid roller cutting plotter can cut a cutting target medium into a desired shape by moving the cutting pen in two-dimensional directions relatively to the cutting target medium.

The flatbed cutting plotter includes a flat plate-like table on which a cutting target medium is placed, a Y bar provided to be movable in the first direction with respect to the table, and a pen block provided to be movable in the second direction perpendicular to the first direction by sliding along the Y bar. The flatbed cutting plotter can cut a cutting target medium into a desired shape by controlling movement of the pen block with respect to the table, and selectively pressing a cutting pen provided in the pen block against the cutting target medium or separating it from the cutting target medium.

Note that the pen block is also called a "head".

A reference mark called a "register mark" is formed in advance on a cutting target medium in order to specify a cuttable region of the cutting target medium. In many cases, the reference mark is constituted by a plurality of line segments, and reference marks are printed in advance at, e.g., the four corners of a cutting target medium.

Some cutting plotters include, in the head, a reflection photosensor (to be simply referred to as a "photosensor" hereinafter) having a light emitting element and a light receiving element, and have a function of automatically detecting a line segment constituting a register mark. The cutting plotter having this function of the line segment detection apparatus irradiates the surface of a cutting target medium with light from the light emitting element while moving the head. The light receiving element receives the light reflected by the surface. The cutting plotter determines whether a register mark is printed, based on the difference between the amount of light reflected by the surface of a portion at which the background color of the cutting target medium is exposed, and the amount of light reflected by the surface of the register mark (see, e.g., Japanese Patent Laid-Open No. 11-114886).

However, the following problems arise when the presence/absence of a register mark is determined based on only the difference between the amount of light reflected by the surface of a portion at which the background color of a cutting target medium is exposed, and the amount of light reflected by the surface of the register mark.

First, when a foreign substance such as a sticky substance is attached on a cutting target medium, the reflected light amount decreases owing to the foreign substance, and the foreign substance may be erroneously detected as a line segment constituting a register mark.

Also, when a cutting target medium 100 has a glossy laminate 102 adhered on a mount 101, as shown in FIG. 1, the surface undulates depending on the state of the cutting target medium 100, and light reflected by the surface of the laminate 102 does not enter the light receiving element, generating a portion at which the luminance level drops. This undulation moves in the moving direction of a photosensor 103 when, for example, a sensor hood 103a of the photosensor 103 moves in contact with the cutting target medium 100. In the case of the grid roller cutting plotter, the cutting target medium 100 tends to curl in the feed direction, and the undulation readily appears as a wrinkle parallel to the Y-axis direction.

At a portion at which the undulation occurs, reflected light does not return to the light receiving element of the sensor 103, and the reflected light amount to the light receiving element greatly decreases. As a result, the portion at which the undulation occurs may be erroneously detected as a line segment constituting a register mark.

Further, when part of the laminate 102 of the cutting target medium 100 is folded, as shown in FIG. 2, even if the folded portion is smoothed by the sensor hood 103a of the photosensor 103 moving together with the head, the folded portion still remains.

If the laminate 102 of the cutting target medium 100 has such a folded portion, most of light reflected by the folded portion does not return to the light receiving element. As a result, the reflected light amount detected by the light receiving element greatly decreases. The folded portion may be erroneously detected as a line segment constituting a register mark.

SUMMARY OF THE INVENTION

The present invention has as its object to provide a line segment detection apparatus and control program capable of detecting a line segment constituting a register mark without the influence of a foreign substance attached on a cutting target medium or the state of a cutting target medium.

To achieve the above object, according to the present invention, there is provided a line segment detection apparatus comprising a head (14) that supports a sensor (16) configured to detect light reflected by a surface of a cutting target medium (2) and output a signal corresponding to an amount of the detected light, a driving unit (17) configured to move the head (14) in two-dimensional directions relatively to the cutting target medium (2), and a processing unit (22, 5) configured to control to drive the driving unit (17) and perform arithmetic processing on an output of the sensor, the processing unit (22, 5) including a detection unit (27b) configured to detect a region (4a, 4b) different in reflectance from surroundings based on a change of a signal output from the sensor (16) when the sensor (16) was moved together with the head (14) in a first direction parallel to the cutting target medium (2), and a determination unit (27c) configured to, when the detection unit (27b) detects the region (4a, 4b), determine whether the region (4a, 4b) is a line segment, based on the change of the signal output from the sensor (16) when the sensor (16) passed an arbitrary point in the region (4a, 4b) and was moved in a second direction parallel to the cutting target medium (2) and perpendicular to the first direction.

According to the present invention, there is provided a computer-readable recording medium recording a control program for a cutting plotter including a head (14) that supports a sensor (16) configured to detect light reflected by a surface of a cutting target medium (2) and output a signal corresponding to an amount of the detected light, a driving unit (17) configured to move the head (14) in two-dimensional directions relatively to the cutting target medium (2), and a processing unit (22, 5) configured to control to drive the driving unit (17) and perform arithmetic processing on an output of the sensor, the control program causing a computer constituting the processing unit (22, 5) to execute the detection step of detecting a region (4a, 4b) different in reflectance from surroundings based on a change of a signal output from the sensor (16) when the sensor (16) was moved together with the head (14) in a first direction parallel to the cutting target medium (2), and the determination step of, when the region (4a, 4b) is detected in the detection step, determining whether the region (4a, 4b) is a line segment, based on the change of the signal output from the sensor (16) when the sensor (16) passed an arbitrary point in the region (4a, 4b) and was moved in a second direction parallel to the cutting target medium (2) and perpendicular to the first direction.

According to the present invention, a line segment is determined based on a change of a signal output from the sensor (16) when the sensor (16) was moved not only in the first direction but also in the second direction. A line segment constituting a register mark can be detected without the influence of a foreign substance attached on a cutting target medium or the state of a cutting target medium.

BRIEF DESCRIPTION OF THE DRAWINGS

FIG. 13 is a graph for explaining the line segment determination processing by the line segment determination unit of the cutting plotter according to the embodiment;

FIG. 14 is a view for explaining line width detection processing by the line width detection unit of the cutting plotter according to the embodiment;

FIG. 15 is a flowchart showing a processing procedure of detecting the first register mark in the cutting plotter according to the embodiment;

DESCRIPTION OF THE PREFERRED EMBODIMENTS

A cutting plotter according to an embodiment of the present invention will now be described with reference to the accompanying drawings.

<Overall Arrangement of Cutting Plotter>

Figure 1:
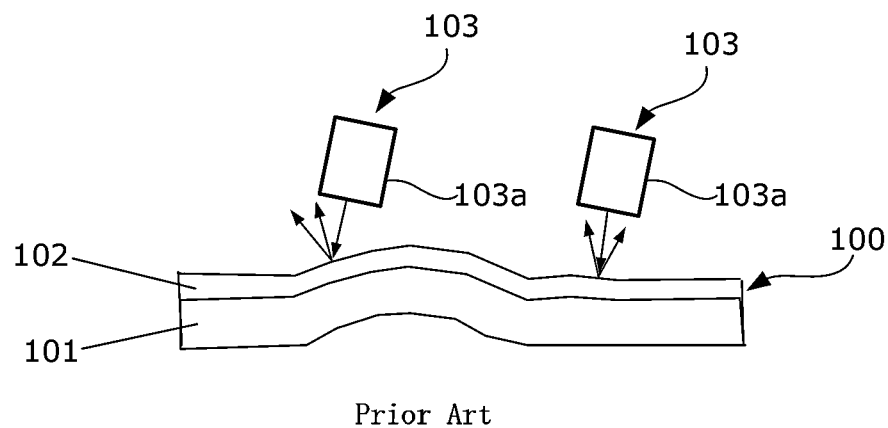
FIG. 1 is a view for explaining a problem in a conventional register mark detection method.
Figure 2:
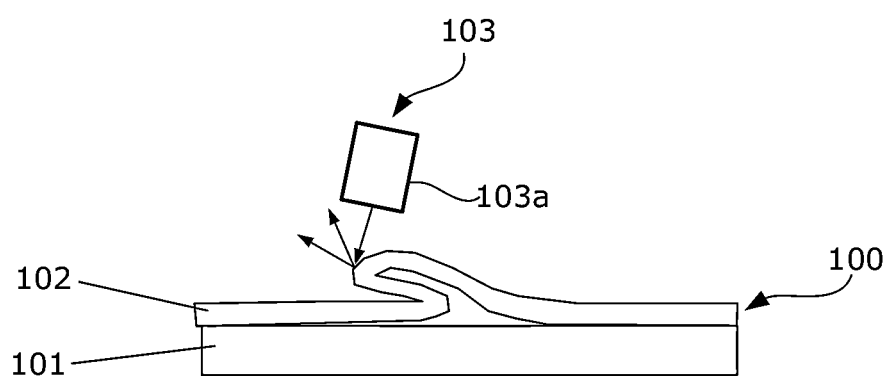
FIG. 2 is a view for explaining a problem in the conventional register mark detection method.
Figure 3:
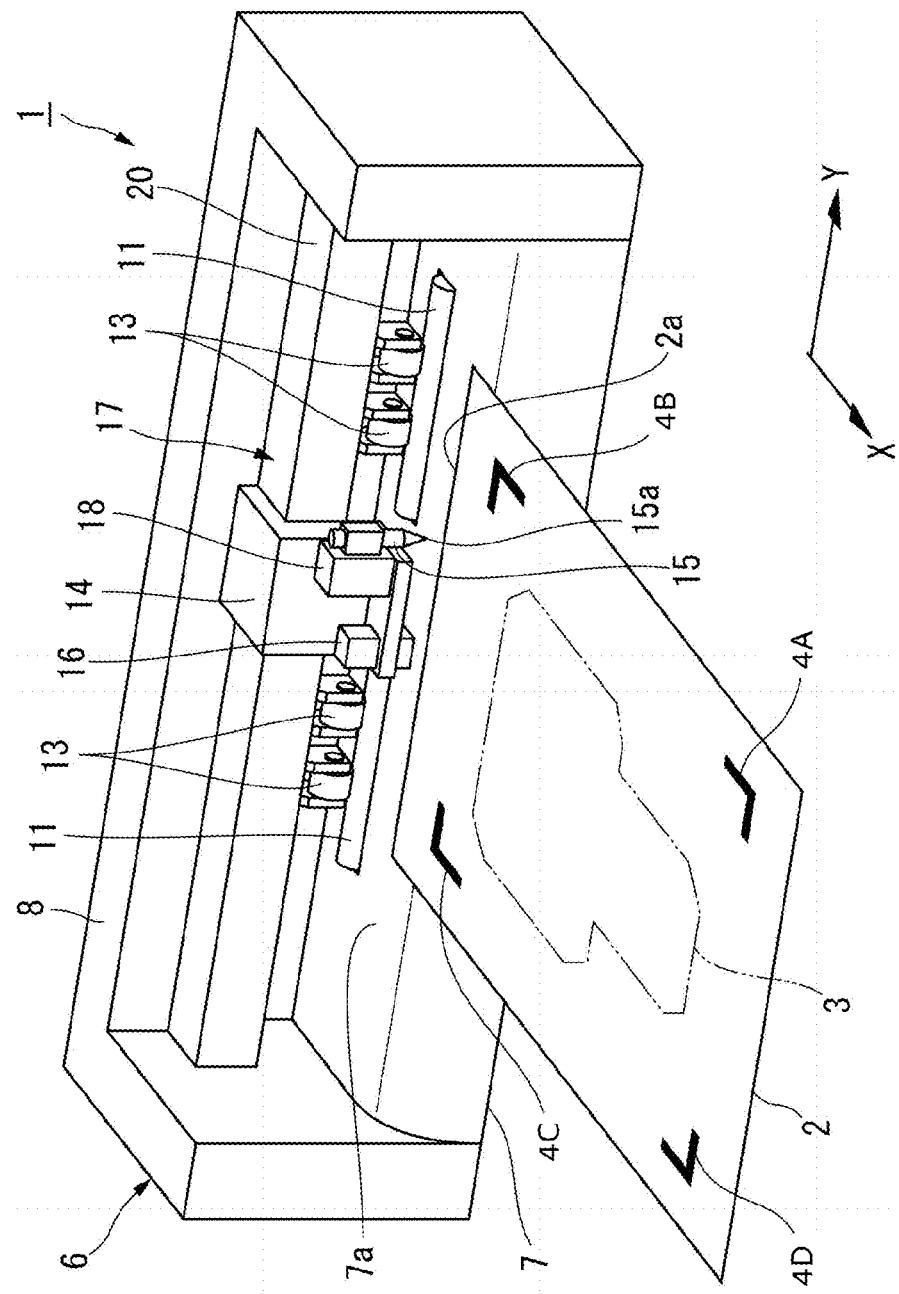
FIG. 3 is a perspective view showing the arrangement of a cutting plotter according to an embodiment of the present invention.

As shown in FIG. 3, a cutting plotter 1 according to the embodiment of the present invention is a grid roller cutting plotter in which a cutting target medium 2 is moved in the first direction by driving rollers 11 and pinch rollers 13 while a head 14 having a cutting pen 15 is moved in the second direction. In this embodiment, the feed direction of the cutting target medium 2 by the driving rollers 11 and the pinch rollers 13, i.e., a direction indicated by an arrow X in FIG. 3 will be referred to as the back-and-forth direction of the cutting plotter 1. A direction perpendicular to the feed direction of the cutting target medium 2, i.e., a direction indicated by an arrow Y in FIG. 3 will be referred to as the left-and-right direction of the cutting plotter 1.

The cutting plotter 1 according to this embodiment is constituted by a cutting plotter main body 6, and a processing unit including various functional units (to be described later).

The cutting plotter main body 6 includes a base 7 on which the cutting target medium 2 is placed, and a guide frame 8 that is spaced apart from the base 7 in directions perpendicular to the back-and-forth direction and the left-and-right direction and extends in the left-and-right direction.

The base 7 has a flat working surface 7a having a rectangular shape long in the left-and-right direction when viewed from the top. The columnar driving rollers 11 each having a rotating shaft extending in the left-and-right direction are supported on the base 7 so that the driving rollers 11 can rotate. Part of the outer surface of each driving roller 11 is exposed from an opening formed in the working surface 7a.

Figure 5:
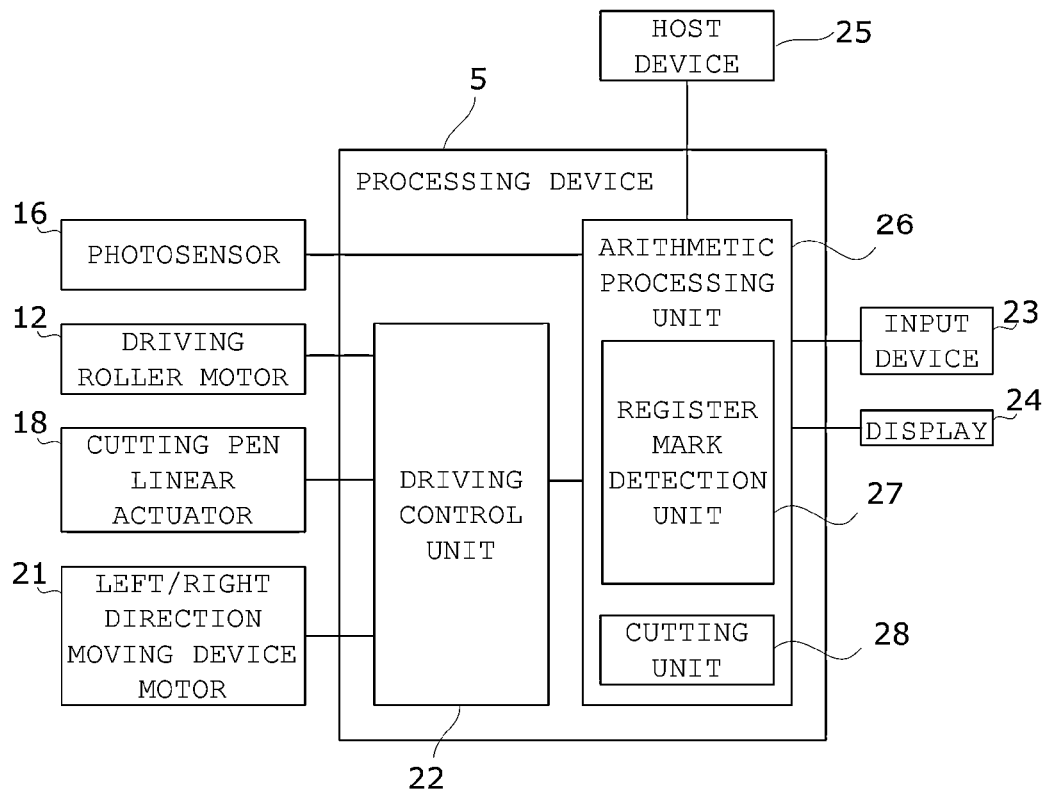
FIG. 5 is a block diagram showing the arrangement of the cutting plotter according to the embodiment.

Each driving roller 11 is coupled to a driving roller motor 12 (see FIG. 5). The driving roller motor 12 is controlled by a processing device 5 (to be described later), and rotates each driving roller 11 clockwise or counterclockwise.

The guide frame 8 is arranged above the working surface 7a of the base 7 at a predetermined interval. The plurality of pinch rollers 13 and the head 14 are provided on the guide frame 8.

The pinch rollers 13 are supported by the guide frame 8 so that they can freely rotate while being biased toward the driving rollers 11. The pinch rollers 13 face the driving rollers 11 and press the cutting target medium 2 against the driving rollers 11. The cutting target medium 2 is clamped between the driving rollers 11 and the pinch rollers 13, and moves forward or backward along with rotation of the driving rollers 11.

Further, the pinch rollers 13 are attached to the guide frame 8 so that they are movable in the left-and-right direction. The user can adjust the attaching positions of the pinch rollers 13 in accordance with the width of the cutting target medium 2 in the left-and-right direction. Although not shown, detection target members may be provided on the pinch rollers 13 to specify the edge positions of the cutting target medium 2 in the left-and-right direction.

The head 14 is supported by the guide frame 8 via a left-and-right direction moving device 17 (to be described later) so that the head 14 is movable in the left-and-right direction.

The head 14 includes the cutting pen 15 serving as a cutter for cutting the cutting target medium 2, and a photosensor 16 formed from a reflection photosensor for detecting register marks 4. A lateral width detection sensor (not shown) may be provided on the head 14 to detect the detection target members of the pinch rollers 13.

The cutting pen 15 is attached to the head 14 via a linear actuator 18 so that it can move up and down. The linear actuator 18 is a power source such as a moving coil or a solenoid, and moves up and down the cutting pen 15 to selectively press and separate it against and from the cutting target medium 2. The processing device 5 (to be described later) controls the operation of the linear actuator 18.

When the cutting pen 15 moves down, a cutting edge 15a provided at the lower end portion of the cutting pen 15 sticks in the cutting target medium 2. When the cutting pen 15 moves up, the cutting edge 15a moves apart from the cutting target medium 2 and retracts above.

The photosensor 16 is attached to the head 14 in a state in which the optical path is oriented down, that is, toward the cutting target medium 2. The photosensor 16 is a well-known reflection photosensor configured to output a signal corresponding to a light amount detected by detecting light reflected by the surface of the cutting target medium 2.

The left-and-right direction moving device 17 is constituted by a guide rail 20 that supports the head 14 so as to freely move it in the left-and-right direction, and a driving mechanism (not shown) that moves the head 14 in the left-and-right direction along the guide rail 20. The driving mechanism can be a mechanism having a structure in which a belt or wire coupled to the head 14 is moved in the left-and-right direction by the power of a left-and-right direction moving device driving roller motor 21 (see FIG. 5).

The processing device 5 serving as a processing unit (to be described later) controls the operation of the driving roller motor 21.

As described above, in the cutting plotter 1, the cutting target medium 2 is moved in the back-and-forth direction by the driving rollers 11 and the pinch rollers 13. In addition, the head 14 is moved in the left-and-right direction by the left-and-right direction moving device 17. The head 14 supporting the cutting pen 15 and the photosensor 16 can therefore be moved in two-dimensional directions relatively to the cutting target medium 2.

<Layout of Cutting Target Medium>

As the cutting target medium 2, a sheet- or roll-like cutting sheet such as paper or a film is usable. This embodiment will exemplify a case in which a sheet-like cutting sheet is used as the cutting target medium 2.

Figure 4:
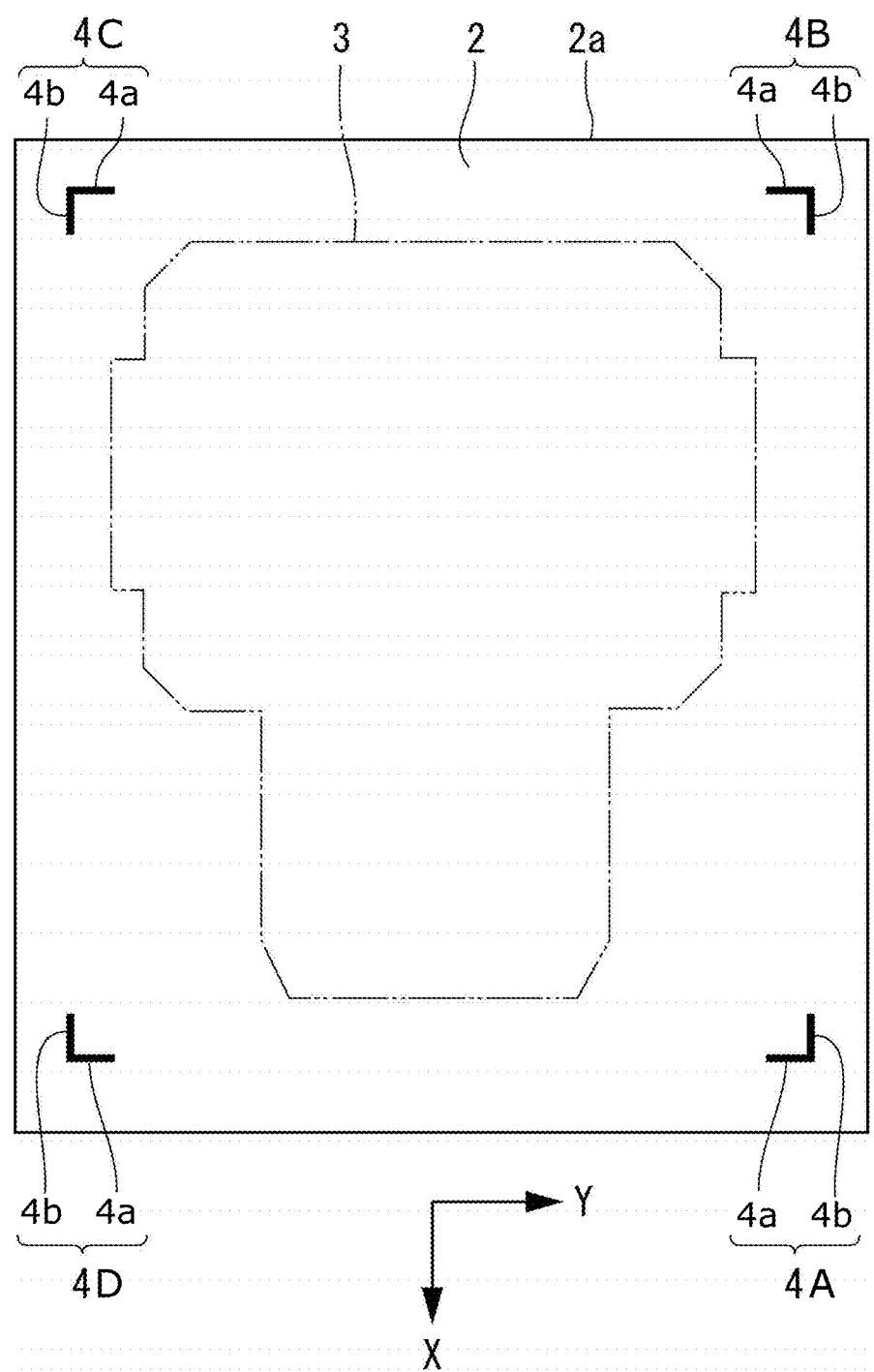
FIG. 4 is a view showing an example of the layout of a cutting target medium.

As shown in FIG. 4, the cutting target medium 2 is a cutting sheet which is rectangular when viewed from the top. Register marks 4A, 4B, 4C, and 4D are printed at the four corners of the cutting target medium 2, respectively.

A "register mark" is a mark serving as a reference to make the contour of a cutting portion 3 such as a figure or character printed on the cutting target medium 2 coincide with a cutting position by the cutting plotter 1. Such register marks are provided at, at least two of the four corners of the cutting target medium 2.

In this embodiment, each of the first register mark 4A, second register mark 4B, third register mark 4C, and fourth register mark 4D provided at the four corners of the cutting target medium 2 is formed into an L shape. More specifically, each of the first register mark 4A, second register mark 4B, third register mark 4C, and fourth register mark 4D is constituted by a first-direction line segment 4a that extends in the widthwise direction (Y direction) of the cutting target medium 2, and a second-direction line segment 4b that extends in the longitudinal direction (X direction) of the cutting target medium 2 and is perpendicular to the first-direction line segment 4a. The first-direction line segment 4a and the second-direction line segment 4b are printed at the same line width and density, and form a black background portion.

Note that the register mark is not limited to the L shape, and marks of various shapes such as a cross shape and an outline rectangular frame are usable as register marks. The arrangements and orientations of these marks are arbitrary. In this embodiment, the register mark has the L shape. However, when the register marks are various patterns, as described above, line segment determination to be described later is performed in accordance with the pattern based on an angle at which two line segments cross each other.

A register mark is generally printed as a black background mark on the cutting target medium 2 of a white background. However, if the cutting target medium 2 has a black background, a register mark of a white background may be printed.

If the luminance differs between the background of the cutting target medium 2 and the line segment of the register mark, the background color of the cutting target medium 2 and the color of the register mark are not limited to specific colors.

<Arrangement of Processing Device of Cutting Plotter>

The cutting plotter 1 according to this embodiment includes the processing device 5 configured to drive a driving unit configured to move the above-described head 14 in two-dimensional directions relatively to the cutting target medium 2, and perform arithmetic processing on an output from the head 14. The processing device 5 is a computer formed from an arithmetic device such as a CPU (Central Processing Unit), a storage device, an interface, and the like. These hardware resources cooperate with a control computer program stored in the storage device to implement a function of cutting the cutting target medium 2 into a desired shape based on externally input graphic data, and a function of automatically detecting the register marks 4 printed on the cutting target medium 2 based on the sensor output of the photosensor 16 mounted on the head 14. That is, the cutting plotter 1 also operates as a line segment detection apparatus.

The processing device 5 of the cutting plotter 1 serving as the line segment detection apparatus will be explained with reference to FIGS. 5 and 6.

As shown in FIG. 5, the processing device 5 includes a driving control unit 22 and an arithmetic processing unit 26.

The driving control unit 22 is configured to move the head 14 in two-dimensional directions relatively to the cutting target medium 2 by driving the driving roller motor 12, the cutting pen linear actuator 18, and the left-and-right direction moving device driving roller motor 21.

The arithmetic processing unit 26 is connected to the photosensor 16, an input device 23, a display device 24, and a host device 25, and is configured to perform arithmetic processing on an output (to be referred to as a "sensor output" hereinafter) from the photosensor 16. The arithmetic processing unit 26 includes a register mark detection unit 27 and a cutting unit 28. The register mark detection unit 27 is a functional unit that detects a register mark based on the sensor output of the photosensor 16. The cutting unit 28 is a functional unit that controls the operation of each device to cut the cutting portion 3 of the cutting target medium 2 based on cutting data supplied from the host device 25.

The input device 23 is a device including a keyboard and a mouse. The operator (not shown) can input various set values via the input device 23, and manually operate the driving rollers 11 and the left-and-right direction moving device 17.

The display device 24 is an output device such as a liquid crystal display (LCD). The display device 24 is used to display various setting contents, and notify the operator of an operating state such as an error or an alarm.

The host device 25 is an external information processing device that inputs cutting data of the cutting target medium 2 to the processing device 5. The host device 25 is constituted by, e.g., a computer.

<Arrangement of Register Mark Detection Unit>

The register mark detection unit 27 includes a region detection unit and a determination unit. The region detection unit is configured to detect a region different in reflectance from the surroundings based on a change of a sensor output from the photosensor 16 when the photosensor 16 was moved together with the head 14 in the first direction parallel to the cutting target medium 2. The determination unit is configured to, when the region detection unit detects a region different in reflectance from the surroundings, determine whether the region different in reflectance from the surroundings is a line segment, based on a change of a sensor output from the photosensor 16 when the photosensor 16 passed an arbitrary point in the region and was moved in the second direction parallel to the cutting target medium 2 and perpendicular to the first direction.

In the following description, moving the photosensor 16 in a direction parallel to the cutting target medium 2 in a state in which a sensor output is obtained, or obtaining a sensor output while moving the photosensor 16 in a direction parallel to the cutting target medium 2 is sometimes called "scan".

Figure 6:
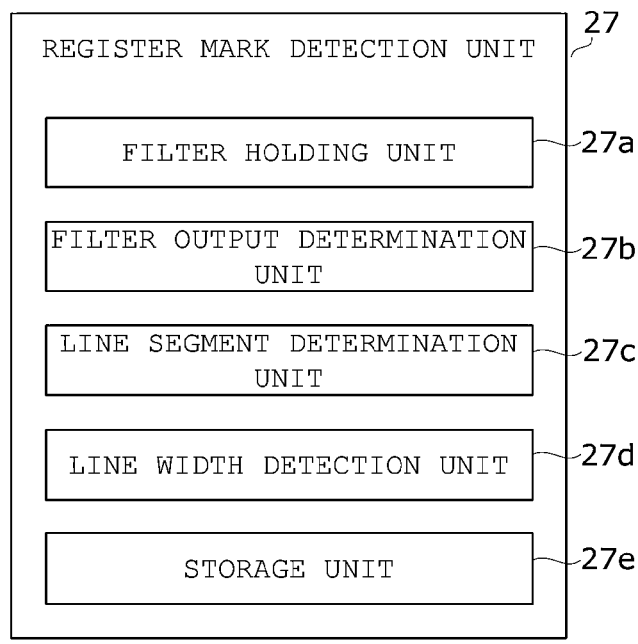
FIG. 6 is a functional block diagram showing the arrangement of the register mark detection unit of the cutting plotter according to the embodiment.

In the cutting plotter 1 according to this embodiment, the register mark detection unit 27 includes a filter holding unit 27a and a filter output determination unit 27b, as shown in FIG. 6. The filter holding unit 27a stores a filter f formed from a rectangular function that takes a predetermined value in a section corresponding to the line width of a line segment to be detected. The filter output determination unit 27b applies the filter f stored in the filter holding unit 27a to the sensor output of the photosensor 16 obtained when the photosensor 16 was moved parallel to the cutting target medium 2 and in the first direction (e.g., X direction). When the filter output exceeds a predetermined threshold, the filter output determination unit 27b determines that a region different in reflectance from the surroundings, i.e., a region lower or higher in reflectance than the background color of the cutting target medium 2 has been detected. The filter holding unit 27a and the filter output determination unit 27b constitute the above-mentioned region detection unit.

The register mark detection unit 27 also includes a line segment determination unit 27c that determines whether a region detected by the filter output determination unit 27b is the line segment (4a or 4b) constituting the register mark 4. A detailed line segment determination processing method by the line segment determination unit 27c will be described later.

Further, the register mark detection unit 27 includes a line width detection unit 27d that detects the line width of a line segment determined as a line segment by the line segment determination unit 27c, and a storage unit 27e that stores values such as various parameters and a line width.

The filter holding unit 27a, filter output determination unit 27b, line segment determination unit 27c, and line width detection unit 27d of the register mark detection unit 27 can be constituted by software using the hardware and computer program of the computer.

The processing device 5 can recognize the register mark 4 only after the register mark detection unit 27 having this arrangement detects both the first-direction line segment 4a and second-direction line segment 4b of one register mark 4.

<Outline of Line Segment Detection Operation>

The operation of the cutting plotter 1 serving as the line segment detection apparatus according to this embodiment includes the following "region detection" and "line segment determination".

(1) Region Detection

First, a region different in reflectance from the surroundings is detected based on a change of a sensor output from the photosensor 16 when the photosensor 16 was moved together with the head 14 in the first direction (e.g., X direction) parallel to the cutting target medium 2.

(2) Line Segment Determination

When a region different in reflectance from the surroundings is detected, whether the region different in reflectance from the surroundings is a line segment is determined based on a change of a sensor output from the photosensor 16 when the photosensor 16 passed an arbitrary point in the region and was moved in the second direction (e.g., Y direction) parallel to the cutting target medium 2 and perpendicular to the first direction.

<Region Detection Operation>

A region detection operation of detecting a region different in reflectance from the surroundings in the detection step will be explained.

In this embodiment, the cross-correlation between the sensor output of the photosensor 16 that moves along the cutting target medium 2, and a function representing a predetermined bright/dark pattern is calculated using the filter f held in the filter holding unit 27a. If an evaluation value serving as the calculation result exceeds a predetermined threshold, it is provisionally determined that the region different in reflectance from the surroundings is a line segment.

The "provisional determination" is provisionally determining, based on a filter output obtained when the filter f was applied to the sensor output of the photosensor 16, that the black background portion of the cutting target medium 2, i.e., a region different in reflectance from the surroundings is the first-direction line segment 4a or second-direction line segment 4b of the register mark 4.

Note that the first-direction line segment 4a or the second-direction line segment 4b is sometimes simply referred to as a "line segment".

<Example of Filter Arrangement>

The filter f at this time is, e.g., a rectangular function that takes a predetermined value in a "dark" section of a predetermined length. As the length of the "dark" section, the line width of the first-direction line segment 4a or second-direction line segment 4b is used. The sensor output of the photosensor 16 that moves along the cutting target medium 2 is a signal representing a change of the reflectance of the surface of the cutting target medium 2. Thus, when the length of a section in which the sensor output of the photosensor 16 drops coincides with the length (line width of the first-direction line segment 4a or second-direction line segment 4b) of a predetermined "dark" section, the evaluation value of the cross-correlation becomes maximum. As the difference between these lengths becomes larger, the evaluation value of the cross-correlation between them becomes smaller.

In the following description, processing of calculating the cross-correlation between the sensor output of the photosensor 16 and the rectangular function including the "dark" section of the predetermined length in the moving direction of the photosensor 16 is sometimes referred to as "filter processing". The functional unit that performs filter processing, or the rectangular function used in filter processing is simply referred to as a "filter" in some cases. The length of the "dark" section is sometimes referred to as a "filter width".

Figure 7:
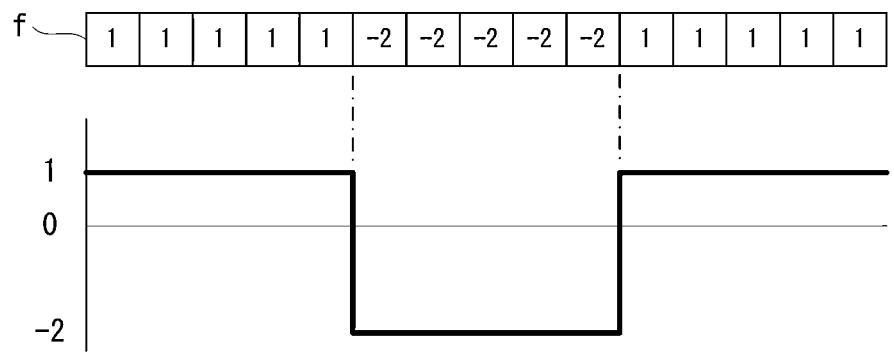
FIG. 7 is a view for explaining an example of a filter used for provisional determination in the cutting plotter according to the embodiment.

FIG. 7 shows an example of a step function including a "dark" section of a predetermined length. This example is an arrangement example of the filter f preferable for provisionally determining a line segment having a line width of five detection pitches.

As shown in FIG. 7, the entire filter f has a width of 15 detection pitches. "−2" representing the "dark" section is assigned to five detection pitches at the center that correspond to the line width of the line segment. "1" representing a "bright" section is assigned to five detection pitches on each of the two sides. By assigning these values, the filter f can change the average value into "0". The filter f can also be expressed as a rectangular function as shown in FIGS. 7.

In this embodiment, the filter holding unit 27a holds a filter f of a default filter width corresponding to the line width of five detection pitches. This filter width can be changed in accordance with the line width (parameter) of a line segment supplied from the line width detection unit 27d, which will be described later.

Instead of changing the filter width, filters f of a plurality of filter widths corresponding to line widths of arbitrary numbers of detection pitches such as a filter f of a filter width corresponding to a line width of three detection pitches and a filter f of a filter width corresponding to a line width of seven detection pitches may be prepared in advance and held.

<Example of Region Detection Operation>

Figure 8:
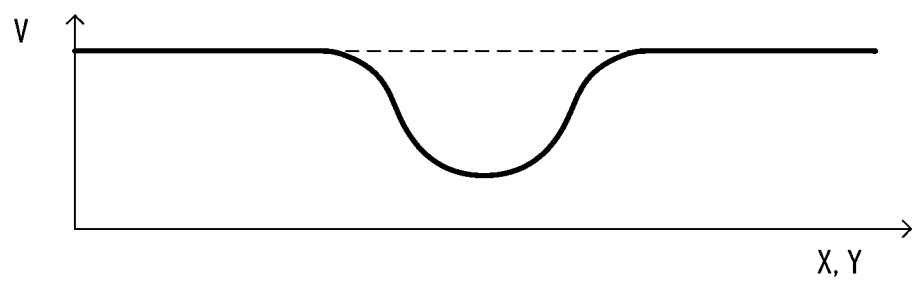
FIG. 8 is a graph showing an example of the sensor output of a photosensor.
Figure 9:
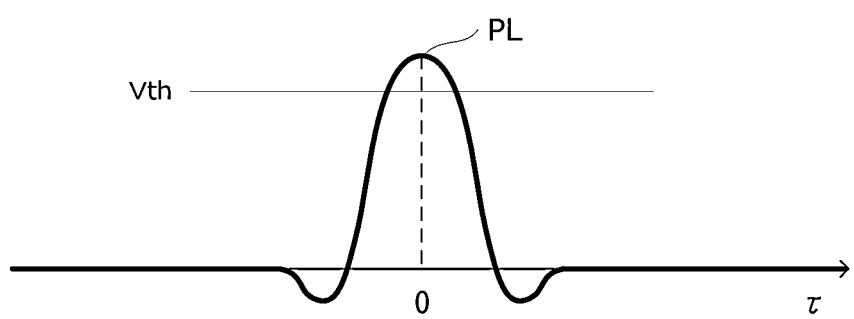
FIG. 9 is a graph showing an example of a filter output obtained by performing filter processing on the output of the photosensor.

For example, when the sensor output of the photosensor 16 as shown in FIG. 8 is obtained, and filter processing is performed by applying the filter f as shown in FIG. 7A to the sensor output, the filter output has a peak PL at the time (τ=0) when the sensor output of the photosensor 16 and the filter f overlap each other at a distance τ (distance in the X or Y direction) between them, as shown in FIG. 9. The height of the peak PL becomes maximum when the line width of a line segment and the filter width of the filter f coincide with each other. As the difference between the line width and the filter width increases, the height of the peak PL decreases.

Figure 10:
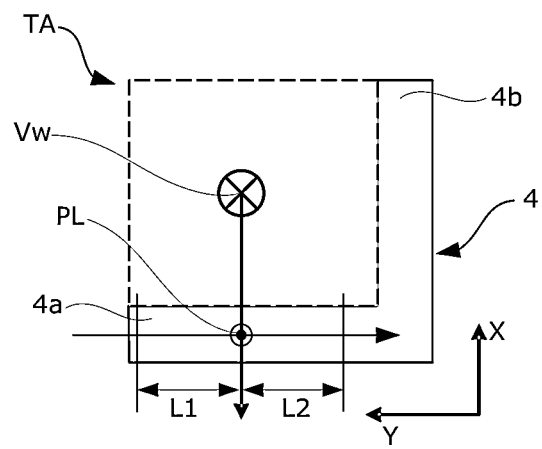
FIG. 10 is a view for explaining line segment determination processing by the line segment determination unit of the cutting plotter according to the embodiment.

As shown in FIG. 10, the filter output determination unit 27b stores in advance, in the storage unit 27e, a value Vw of the sensor output obtained when the photosensor 16 positioned in a rectangular register mark region TA including the register mark 4 read out a white background portion (indicated by a x mark), as shown in FIG. 10.

The filter output determination unit 27b sequentially calculates filter outputs by applying the filter f held in the filter holding unit 27a while shifting, by every detection pitch, a sensor output obtained when the photosensor 16 scanned the register mark region TA to cross the black background portion in the X direction serving as the first direction. Accordingly, the filter output determination unit 27b obtains the cross-correlation between the sensor output of the photosensor 16 and the filter f.

If the peak PL of the filter output representing the cross-correlation between the sensor output of the photosensor 16 and the filter f has exceeded a preset threshold Vth, as shown in FIG. 9, the filter output determination unit 27b provisionally determines that a region of the cutting target medium 2 equivalent to a filter width including a position corresponding to the peak PL is the first-direction line segment 4a.

Note that the state in which the peak PL of the filter output of the filter f has exceeded the threshold Vth means that a region (a region lower in reflectance than the surroundings is sometimes referred to as a "black background portion" hereinafter) lower in reflectance than the white background portion of the cutting target medium 2 has been detected in a section equivalent to the filter width.

The filter output determination unit 27b stores, in the storage unit 27e, the coordinate value of the peak PL obtained when the peak PL of the filter output has exceeded the threshold Vth. Note that the filter output determination unit 27b performs the above-described provisional determination not only for the first-direction line segment 4a, but also for the second-direction line segment 4b constituting the register mark 4.

If the filter output determination unit 27b detects that the peak PL of the filter output has not exceeded the threshold Vth, it determines that the black background portion of the cutting target medium 2 is neither the first-direction line segment 4a nor the second-direction line segment 4b and is dust, a wrinkle of the cutting target medium 2, or the like. Thus, the filter output determination unit 27b can exclude dust, a wrinkle of the cutting target medium 2, and the like from line segment detection targets at the initial stage when detecting the first-direction line segment 4a constituting the register mark 4.

<Line Segment Determination Operation>

When the filter output determination unit 27b provisionally determines that the black background portion of the cutting target medium 2, that is, the region different in reflectance from the surroundings is a line segment, the driving control unit 22 controls the driving unit so that the photosensor 16 mounted on the head 14 passes a position corresponding to the peak PL of the filter output and moves in the Y direction. The storage unit 27e stores sensor outputs (serial data) obtained when the photosensor 16 scanned a first scan section L1 and second scan section L2 defined in advance as target ranges of line segment determination, as shown in FIG. 10.

The first scan section L1 and the second scan section L2 are set in two directions along the Y direction from a center start point that is a position corresponding to the peak PL of the filter output obtained upon scanning first in the X direction.

In the example shown in FIG. 10, the first scan section L1 and the second scan section L2 are set in the longitudinal direction of the first-direction line segment 4a of the register mark 4. When the photosensor 16 scans the first scan section L1 and the second scan section L2, this means scanning on the first-direction line segment 4a.

Based on a sensor output obtained when the first scan section L1 and the second scan section L2 were scanned in the Y direction, the line segment determination unit 27c determines whether the black background portion of the cutting target medium 2 that has been provisionally determined as a line segment by the filter output determination unit 27b is a line segment.

As an example of this line segment determination processing, the following three types (1) to (3) of line segment determination processing will be explained.

(1) Example in Which Average Value and Standard Deviation of Sensor Output Are Used The first line segment determination processing is a method of verifying a change of the reflectance of the cutting target medium 2 in the Y direction by using the standard deviation of a sensor output obtained when the photosensor was scanned in the Y direction.

Figure 11:
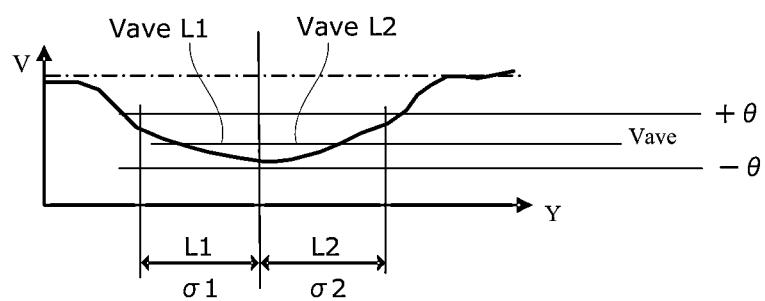
FIG. 11 is a graph for explaining the line segment determination processing by the line segment determination unit of the cutting plotter according to the embodiment.

As shown in FIG. 11, the line segment determination unit 27c calculates, for the first scan section L1 and the second scan section L2, average values VaveL1 and VaveL2 of sensor outputs obtained when the photosensor 16 scanned the first scan section L1 and the second scan section L2, and standard deviations σ1 and σ2 of the sensor outputs, respectively.

After the standard deviations σ1 and σ2 are calculated, the line segment determination unit 27c determines whether the average value Vave L1 and standard deviation ±σ1 of sensor outputs in the first scan section L1 fall within predetermined ranges, respectively. Similarly, the line segment determination unit 27c determines whether the average value VaveL2 and standard deviation ±σ2 of sensor outputs of the photosensor 16 in the second scan section L2 fall within predetermined ranges, respectively.

For example, a case will be examined, in which when the sensor output of the photosensor 16 has W tones, a sensor output of the photosensor 16 for the white background portion of the cutting target medium 2 is "W" equivalent to the value Vw of the sensor output stored in advance in the storage unit 27e, and a sensor output of the photosensor 16 for the black background portion is, e.g., "2W/3".

If the black background portion is the first-direction line segment 4a, the black high-density region continues in the Y direction, and the sensor output is considered to continue around a value corresponding to the black high-density region, i.e., "2W/3" in the Y direction (to be referred to as "smoothness of the sensor output" hereinafter). If the average values VaveL1 and VaveL2 of sensor outputs of the photosensor 16 in both the first scan section L1 and the second scan section L2 exist near the sensor output "2W/3" and the values of the standard deviations ±σ1 and ±σ2 fall within the predetermined ranges, it can be considered that the smoothness of the sensor output has been verified.

From this, if the average values VaveL1 and VaveL2 of sensor outputs of the photosensor 16 in both the first scan section L1 and the second scan section L2 exist near the sensor output "2W/3" and the values of the standard deviations ±σ1 and ±σ2 fall within the arbitrary ranges, the line segment determination unit 27c can be determined that the black background portion is the first-direction line segment 4a constituting the register mark 4.

In this embodiment, however, if the average value VaveL1 or VaveL2 of sensor outputs of the photosensor 16 in either the first scan section L1 or the second scan section L2 exists near the sensor output "2W/3" and the value of the standard deviation ±σ1 or ±σ2 falls within the predetermined range, the line segment determination unit 27c determines that the black background portion is the first-direction line segment 4a.

The reason is as follows.

When the cutting target medium 2 is placed on the base 7 while being slightly rotated clockwise or counterclockwise, the first-direction line segment 4a constituting the register mark 4 is also slightly inclined in the X and Y directions. In this case, if the photosensor 16 passes the above-mentioned position corresponding to the peak PL of the filter output and scans both the first scan section L1 and the second scan section L2 in the Y direction, the average value VaveL1 or VaveL2 of sensor outputs of the photosensor 16 may exist near the sensor output "2W/3" in only either the first scan section L1 or the second scan section L2.

Thus, even when the average value VaveL1 or VaveL2 of sensor outputs exists near the sensor output "2W/3" in only either the first scan section L1 or the second scan section L2, but the value of the standard deviation ±σ1 or ±σ2 falls within the predetermined range, the line segment determination unit 27c determines that the black background portion provisionally determined as a line segment is a line segment. Accordingly, even when the cutting target medium 2 is placed obliquely in the X and Y directions, the first-direction line segment 4a constituting the register mark 4 can be detected without missing it.

(2) Example in Which Peak Value of Sensor Output Is Used

As described above, if the average value VaveL1 and/or VaveL2 of sensor outputs of the photosensor 16 exists near the sensor output "2W/3" in both or either of the first scan section L1 and second scan section L2, and the value of the standard deviations ±σ1 and/or ±σ2 falls within the arbitrary range, the line segment determination unit 27c determines that the black background portion is the first-direction line segment 4a.

Figure 12:
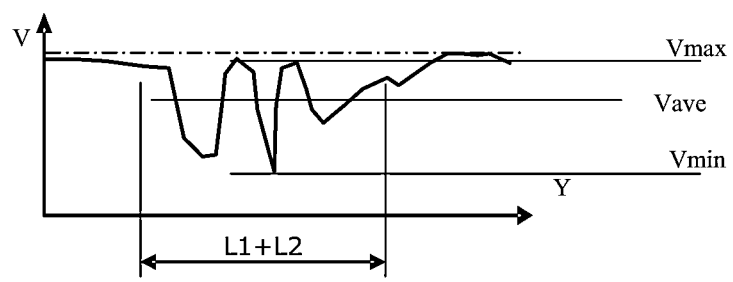
FIG. 12 is a graph for explaining the line segment determination processing by the line segment determination unit of the cutting plotter according to the embodiment.

However, if the peak of the sensor output of the photosensor 16 is equal to or larger than a predetermined upper limit value Vmax (Vmax≥λmax·Vave) larger than the average value Vave of the sensor output, or the peak of the sensor output is equal to or smaller than a predetermined lower limit value Vmin (Vmin λmin·Vave) smaller than the average value Vave of the sensor output, as shown in FIG. 12, the line segment determination unit 27c determines that the black background portion is not a line segment. This is because in this case, the sensor output does not have satisfactory smoothness, the high-density region of the black background portion is discontinuous, and the black background portion is highly likely to be dust or a wrinkle of the cutting target medium 2.

Here, λmax and λmin are arbitrary coefficients that satisfy λmax≥1.0 and λmin<1.0, respectively.

(3) Example of Comparison with White Background Portion

As shown in FIGS. 10 and 13, the line segment determination unit 27c compares the value Vw of a sensor output of the photosensor 16 for the white background portion of the cutting target medium 2 with a sensor output of the photosensor 16 at a line segment detection start point SP in the Y direction that corresponds to the peak PL of the filter output of the filter f. If the sensor output at the line segment detection start point SP in the Y direction is close to the value Vw of the sensor output for the white background portion, that was obtained when the sensor was calibrated as described later, then the line segment determination unit 27c determines that the black background portion is not the first-direction line segment. If the sensor output at the line segment detection start point SP in the Y direction is much smaller than the value Vw of the sensor output for the white background portion, meanwhile, the line segment determination unit 27c determines that the black background portion is the first-direction line segment 4a. In this case, the line segment determination unit 27c may further perform at least one of the line segment determination processes described in (1) and/or (2) above.

At the initial stage at which none of the first to fourth register marks 4A to 4D have been determined yet, there is no white/black determination value serving as a criterion for determining whether the sensor output of the photosensor 16 is much smaller than the value Vw of the sensor output for the white background portion. Hence, the line segment determination unit 27c multiplies the value Vw of the sensor output for the white background portion by a predetermined coefficient k, and sets k·Vw as a default white/black determination value. If a sensor output of the photosensor 16 at the line segment detection start point SP is equal to or smaller than this white/black determination value, the line segment determination unit 27c determines that the black background portion is the first-direction line segment 4a. Here, k is an arbitrary positive coefficient smaller than 1.0.

After determining that the black background portion constitutes the first register mark 4A, the line segment determination unit 27c sets a value WB obtained by the following equation as a new white/black determination value, and performs white/black determination of the first-direction line segment 4a:

$$WB=Av+(Vw-Av)/2$$

where Av is a smaller one of an average value Av1 of sensor outputs of the photosensor 16 in the first scan section L1 and an average value Av2 of sensor outputs of the photosensor 16 in the second scan section L2.

In this manner, after determining the first register mark 4A, the new white/black determination value WB representing an intermediate level between the value Vw of the sensor output for the white background portion and the average value Av (a smaller one of Av1 and Av2) of sensor outputs of the photosensor 16 can be calculated. If a sensor output of the photosensor 16 at the line segment detection start point SP is smaller than the new white/black determination value WB, the line segment determination unit 27c determines that the black background portion is the first-direction line segment 4a; otherwise, the line segment determination unit 27c determines that the black background portion is not the first-direction line segment 4a.

In the cutting plotter 1 according to this embodiment, the line segment determination unit 27c executes all the above-described methods (1) to (3), and if the conditions are satisfied in all the methods, determines that the black background portion is the first-direction line segment 4a.

Based on one of the results in (1) to (3), the line segment determination unit 27c may determine that the black background portion is the first-direction line segment 4a.

The line segment determination unit 27c may combine arbitrary two of (1) to (3) and determine whether the black background portion is the first-direction line segment 4a.

<Processing by Line Width Detection Unit>

The line width detection unit 27d detects the line widths of the first-direction line segment 4a and second-direction line segment 4b that have been determined as line segments by the line segment determination unit 27c.

When the black background portion is determined as, e.g., the first-direction line segment 4a, the driving control unit 22 controls the driving unit so that the photosensor 16 performs scanning again in the first direction (X direction) to cross the first-direction line segment 4a from the white background portion (indicated by the x mark) of the register mark region TA. The line width detection unit 27d differentiates sensor outputs at this time, obtaining two peaks as shown in FIG. 14.

The line width detection unit 27d detects a line width h based on the interval between these two peaks, and stores the value of the line width h in the storage unit 27e. The value of the line width h is output as a parameter to the filter holding unit 27a.

Note that the line width detection unit 27d similarly detects the line width h of the second-direction line segment 4b.

By the above-described processing, a black background portion is detected, and it is determined whether the detected black background portion is a line segment.

<Register Mark Detection Operation of Cutting Plotter>

Next, a register mark detection operation of detecting the plurality of register marks 4A to 4D printed on the cutting target medium 2 in the cutting plotter 1 having the above-described arrangement will be explained separately as the first register mark detection operation of detecting the first register mark, and the second to fourth register mark detection operations after detecting the first register mark.

<First Register Mark Detection Operation>

Before entering a detection operation for the first register mark 4A, the processing device 5 performs gain adjustment (calibration) of the photosensor 16 for the white background portion of the cutting target medium 2. This can compensate for the error of the photosensor 16 with respect to the luminance level of the white background portion of each cutting target medium 2.

As shown in FIG. 15, when automatic line segment detection processing starts, the processing device 5 first starts scanning to cross the first-direction line segment 4a constituting the first register mark 4A by moving the photosensor 16 in the first direction, e.g., the X direction from a start point near the first register mark 4A (step S01). At this time, the start point is, e.g., the white background portion (indicated by the x mark) of the register mark region TA, as shown in FIG. 10. Note that the processing device 5 can automatically detect the register mark region TA by moving the photosensor 16 spirally with respect to the cutting target medium 2 until the first-direction line segment 4a is detected.

The processing device 5 applies the filter f held in the filter holding unit 27a to the sensor output of the photosensor 16, and performs provisional determination based on the filter output (step S02).

Since the first register mark 4A has not been detected yet at this stage, a filter f having a filter width of five detection pitches, which is a default filter, is applied to the sensor output. If the peak PL of the filter output of the filter f exceeds the default threshold Vth, the processing device 5 provisionally determines that the black background portion of the cutting target medium 2 is the first-direction line segment 4a. In addition, the processing device 5 stores, in the storage unit 27e, the coordinate value of a position corresponding to the peak PL of the filter output.

Figure 16:
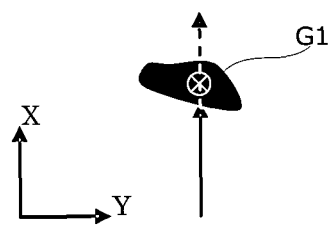
FIG. 16 is a view for explaining provisional determination processing in the cutting plotter according to the embodiment.

If the black background portion is dust, as shown in FIG. 16, the black background portion can be excluded as dust or the like unless the peak PL (see FIG. 9) of the filter output exceeds the default threshold Vth. However, if the peak PL of the filter output exceeds the default threshold Vth, as shown in FIG. 9, the processing device 5 provisionally determines that this black background portion is the first-direction line segment 4a.

If the black background portion is provisionally determined as the first-direction line segment 4a in step S02, the processing device 5 executes line segment determination processing on the black background portion (step S03).

More specifically, the processing device 5 moves the photosensor 16 in the second direction, i.e., the Y direction via the driving control unit 22. The photosensor 16 passes a position of the photosensor 16 that corresponds to the peak PL of the filter output, and scans both the first scan section L1 and the second scan section L2 in the Y direction.

The processing device 5 executes all the above-described verification methods (1) to (3) for the sensor output obtained as a result of scanning the scan sections. If the conditions are satisfied in all (1) to (3), the processing device 5 determines that the black background portion is the first-direction line segment 4a constituting the first register mark 4A. If the condition is not satisfied in any one of the verification methods, the processing device 5 determines that the black background portion is not the first-direction line segment 4a.

Figure 17:
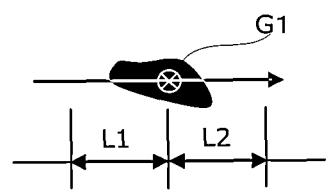
FIG. 17 is a view for explaining the line segment determination processing by the line segment determination unit of the cutting plotter according to the embodiment.

At this time, even if dust G1 is provisionally determined as the first-direction line segment 4a in step S02, the processing device 5 verifies the smoothness by using the standard deviations of sensor outputs in the above-described method (1) for the first scan section L1 and second scan section L2 including one point in the black background portion, as shown in FIG. 17.

In this case, the dust G1 does not have the continuity of a high-density region in both the first scan section L1 and the second scan section L2, unlike a line segment. Even if the average values VaveL1 and VaveV2 of sensor outputs of the photosensor 16 exist near the sensor output "2W/3", the values of the standard deviations ±σ1 and ±σ2 do not fall within the predetermined ranges. Thus, the processing device 5 can determine that the dust G1 is not the first-direction line segment 4a.

If the processing device 5 determines as a result of line segment determination (step S03) that the black background portion is not the first-direction line segment 4a, the process returns to step S01 (step S04: NO) to repeat the above-described processing. To the contrary, if the processing device 5 determines that the black background portion is the first-direction line segment 4a, the process shifts to the next step S05 (step S04: YES).

If the processing device 5 determines in step S04 that the black background portion is the first-direction line segment 4a, it detects the line width of the first-direction line segment 4a (step S05).

Figure 18:
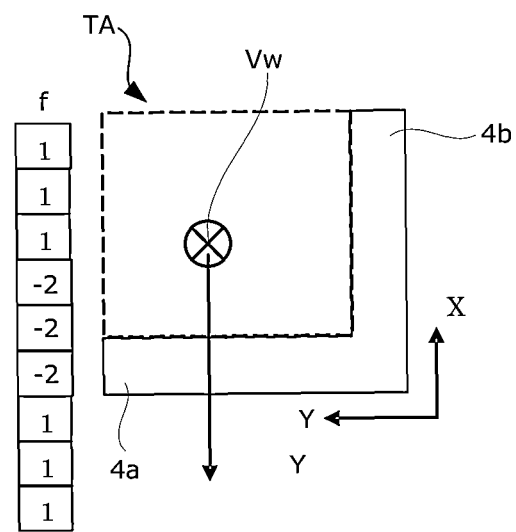
FIG. 18 is a view for explaining register mark detection processing using a filter.

More specifically, the processing device 5 scans again the photosensor 16 via the driving control unit 22 in the X direction from a start point in the white background portion (indicated by the x mark) of the register mark region TA, as shown in FIG. 18. The line width detection unit 27d detects the line width h (for example, three detection pitches) of the first-direction line segment 4a from the sensor output at this time, and stores it in the storage unit 27e.

After obtaining the line width h of the first-direction line segment 4a, the processing device 5 constitutes a filter f of a filter width (three detection pitches) corresponding to the line width h of the first-direction line segment 4a, as shown in FIG. 18, and holds it in the filter holding unit 27a.

Figure 19:
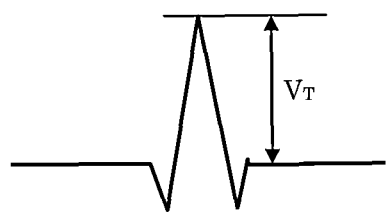
FIG. 19 is a chart for explaining the register mark detection processing using the filter.

The processing device 5 applies the filter f to a sensor output of the photosensor 16 obtained when the photosensor 16 was scanned again in the X direction via the driving control unit 22, as shown in FIG. 19. The processing device 5 calculates a threshold VTX by multiplying a peak VT of the obtained filter output by a predetermined coefficient $\alpha(0<\alpha<1.0)$, and stores the threshold VTX in the storage unit 27e (step S06). The threshold VTX is used as a criterion in the filter output determination unit 27b for provisional determination of the first-direction line segment 4a constituting the next second register mark 4B.

Since it has already been determined that the black background portion is the first-direction line segment 4a, the processing device 5 then performs a detection operation for detecting the second-direction line segment.

More specifically, first, the processing device 5 moves the photosensor 16 via the driving control unit 22 to cross the second-direction line segment 4b in the Y direction from a start point in the white background portion (indicated by the x mark) of the register mark region TA.

At this time, the processing device 5 applies the default filter f (filter width of five detection pitches) held in the filter holding unit 27a to the sensor output of the photosensor 16, as in the case of the first-direction line segment 4a. If the peak PL of the filter output of the filter f exceeds the default threshold Vth, the processing device 5 provisionally determines that the black background portion at this time is the second-direction line segment 4b (step S07).

If the processing device 5 provisionally determines in step S07 that the black background portion is the second-direction line segment 4b, it executes line segment determination processing on the black background portion (step S08).

More specifically, the processing device 5 moves the photosensor 16 in the first direction, i.e., the X direction via the driving control unit 22. The photosensor 16 passes a position of the photosensor 16 that corresponds to the peak PL of the filter output, and scans both the first scan section L1 and the second scan section L2 in the X direction.

The processing device 5 executes all the above-described verification methods (1) to (3) for the sensor output obtained as a result of scanning the scan sections. If the conditions are satisfied in all (1) to (3), the processing device 5 determines that the black background portion is the second-direction line segment 4b constituting the first register mark 4A. If the condition is not satisfied in any one of the verification methods, the processing device 5 determines that the black background portion is not the second-direction line segment 4b.

If the processing device 5 determines in step S08 that the black background portion is not the second-direction line segment 4b (step S09: NO), it displays an error on the display device 24 (step S10), and ends the process.

If the processing device 5 determines in step S08 that the black background portion is the second-direction line segment 4b (step S09: YES), the process shifts to the next step S11.

In step S11, the processing device 5 finally recognizes the first register mark 4A constituted by the first-direction line segment 4a and the second-direction line segment 4b (step S11), and the process shifts to the next step S12.

If the processing device 5 determines in step S08 that the black background portion is the second-direction line segment 4b, it detects the line width of the second-direction line segment 4b (step S12).

In step S12, the processing device 5 scans again the photosensor 16 via the driving control unit 22 in the Y direction from a start point in the white background portion (indicated by the x mark) of the register mark region TA. The processing device 5 causes the line width detection unit 27d to detect the line width h (for example, three detection pitches) of the second-direction line segment 4b from the sensor output at this time, and stores the line width h in the storage unit 27e.

The processing device 5 scans again the photosensor 16 in the Y direction via the driving control unit 22. The filter holding unit 27a applies, to the obtained sensor output, the filter f obtained by changing the filter width in accordance with the line width h (three detection pitches) of the second-direction line segment 4b. The processing device 5 calculates a threshold VTY from the peak VT (see FIG. 19) of the filter output at this time, stores it in the storage unit 27e (step S13), and ends the process.

As a detailed calculation method of the threshold VTY, the processing device 5 calculates the threshold VTY by multiplying the peak VT of the filter output as shown in FIG. 19 by a coefficient β(β<1.0), and stores the threshold VTY in the storage unit 27e. The threshold VTY is used as a criterion in the filter output determination unit 27b for provisional determination of the second-direction line segment 4b constituting the next second register mark 4B.

By using the filter f of a default filter width and the default threshold Vth, the processing device 5 provisionally determines whether detected black background portions are the first-direction line segment 4a and second-direction line segment 4b constituting the first register mark 4A. After that, the processing device 5 determines the continuity of the density of the black background portion by the line segment determination unit 27c based on smoothness verification using (1) the standard deviation of the sensor output and (2) the peak value of the sensor output. Further, the processing device 5 determines the color (white background portion or black background portion) of the line segment by verification of the black background portion based on (3) comparison with the white background portion by the line segment determination unit. Hence, while preventing detection of dust, a wrinkle of the cutting target medium 2, or the like as a line segment even for the first register mark 4A, the first-direction line segment 4a or second-direction line segment 4b constituting the first register mark 4A can be accurately detected as a line segment.

<Detection Operation for Second to Fourth Register Marks>

Figure 21:
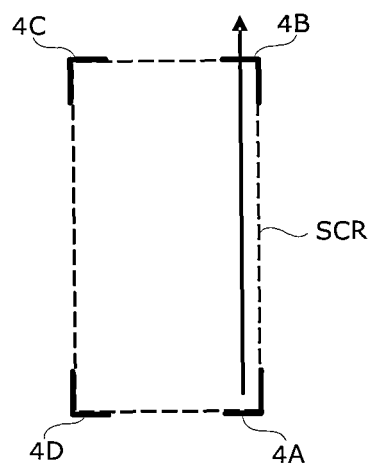
FIG. 21 is a view for explaining an operation when searching for the second register mark from the first register mark.
Figure 22:
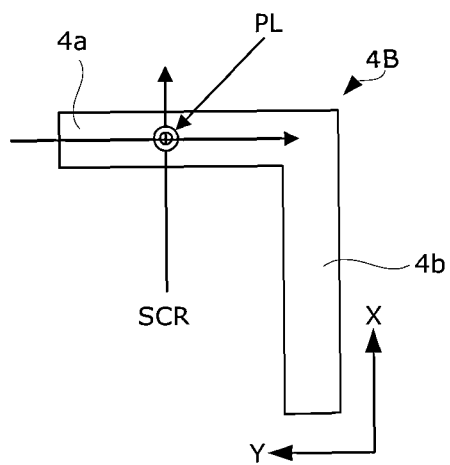
FIG. 22 is a view for explaining the line segment determination processing by the line segment determination unit.
Figure 20:
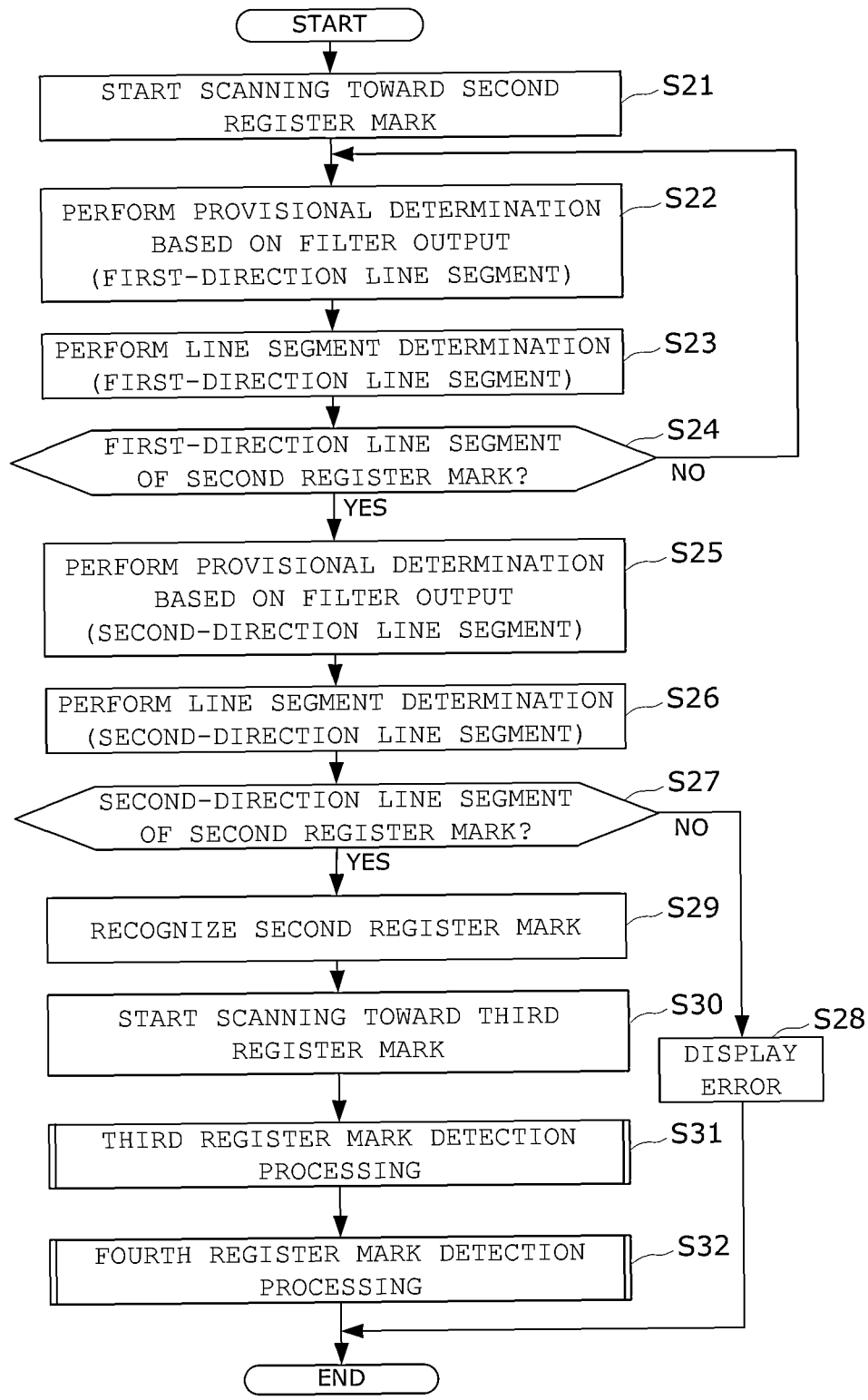
FIG. 20 is a flowchart showing a processing procedure of detecting the second and subsequent register marks in the cutting plotter according to the embodiment.

An operation of detecting the second, third, and fourth register marks 4B, 4C, and 4D after detecting the first register mark 4A will be explained with reference to FIGS. 20, 21, and 22.

After detecting the first register mark 4A, the processing device 5 moves the photosensor 16 via the driving control unit 22 to scan it from the first register mark 4A to the second register mark 4B (step S21). For example, the photosensor 16 scans along a search path SCR from the first register mark 4A to the second register mark 4B, as shown in FIG. 21.

Based on a filter output obtained when the filter f was applied to the sensor output at this time, the processing device 5 performs provisional determination of the first-direction line segment in the Y direction that constitutes the second register mark 4B (step S22). At this time, the line width h of the first-direction line segment 4a constituting the second register mark 4B is equal to the line width h of the first-direction line segment 4a constituting the first register mark 4A. Thus, the filter holding unit 27a applies, to the sensor output, a filter f of a filter width corresponding to the line width h of the first-direction line segment 4a constituting the first register mark 4A, which filter f is stored in the storage unit 27e.

If the peak PL of the filter output of the filter f has exceeded the threshold VTX stored in the storage unit 27e, as shown in FIG. 9, the processing device 5 provisionally determines that the black background portion of the cutting target medium 2 is the first-direction line segment 4a constituting the second register mark 4B. In addition, the processing device 5 stores the coordinate value of a position corresponding to the peak PL in the storage unit 27e.

If the processing device 5 provisionally determines in step S22 that the detected black background portion is the first-direction line segment in the Y direction that constitutes the second register mark 4B, it performs line segment determination of the first-direction line segment (step S23).

More specifically, the processing device 5 moves the photosensor 16 via the driving control unit 22. The photosensor 16 passes a position corresponding to the peak PL of the filter output of the filter f, and scans both the first scan section L1 and the second scan section L2 (see FIG. 22) in the longitudinal direction of the first-direction line segment 4a, i.e., the Y direction, as in the case of the first register mark 4A. verification methods (1) to (3) for sensor The processing device 5 executes all the above-described outputs obtained by scanning the first scan section L1 and the second scan section L2. If the conditions are satisfied in all (1) to (3), the processing device 5 determines that the black background portion is the first-direction line segment 4a constituting the second register mark 4B. If the condition is not satisfied in any one of the verification methods, the processing device 5 determines that the black background portion is not the first-direction line segment 4a.

If the processing device 5 determines in step S23 that the black background portion is not the first-direction line segment 4a constituting the second register mark 4B (step S24: NO), the process returns to step S22 to repeat the provisional determination (step S22) and the line segment determination (step S23) for the first-direction line segment of the second register mark. If the processing device 5 determines in step S23 that the black background portion is the first-direction line segment 4a constituting the second register mark 4B (step S24: YES), the process advances to step S25.

If the first-direction line segment 4a constituting the second register mark 4B is detected, the processing device 5 then executes an operation for detecting the second-direction line segment 4b constituting the second register mark 4B.

More specifically, the processing device 5 moves the photosensor 16 via the driving control unit 22 in the Y direction so that the photosensor 16 crosses the second-direction line segment 4b. The processing device 5 applies the filter f held in the filter holding unit 27a to the sensor output of the photosensor 16, as in the case of the first-direction line segment 4a. Based on the filter output of the filter f, the processing device 5 performs provisional determination of the second-direction line segment 4b in the X direction that constitutes the second register mark 4B (step S25).

At this time, the line width h of the second-direction line segment 4b constituting the second register mark 4B is equal to the line width h of the second-direction line segment 4b constituting the first register mark 4A. Thus, the filter holding unit 27a applies, to the sensor output, a filter f of a filter width corresponding to the line width h of the second-direction line segment 4b constituting the first register mark 4A, which filter f is stored in the storage unit 27e.

If the peak PL of the filter output has exceeded the threshold VTY stored in the storage unit 27e, as shown in FIG. 9, the processing device 5 provisionally determines that the black background portion of the cutting target medium 2 is the second-direction line segment 4b constituting the second register mark 4B. At the same time, the processing device 5 stores the coordinate value of a position corresponding to the peak PL of the filter output in the storage unit 27e.

If the processing device 5 provisionally determines that the black background portion of the cutting target medium 2 is the second-direction line segment 4b constituting the second register mark 4B, it performs line segment determination of the second-direction line segment (step S26).

More specifically, the processing device 5 moves the photosensor 16 via the driving control unit 22. The photosensor 16 passes a position corresponding to the peak PL of the filter output of the filter f, and scans both the first scan section L1 and the second scan section L2 in the longitudinal direction of the first-direction line segment 4a, i.e., the Y direction, as in the case of the first register mark 4A.

The processing device 5 executes all the above-described verification methods (1) to (3) for sensor outputs obtained by scanning the first scan section L1 and the second scan section L2. If the conditions are satisfied in all (1) to (3), the processing device 5 determines that the black background portion is the second-direction line segment 4b constituting the second register mark 4B. If the condition is not satisfied in any one of the verification methods, the processing device 5 determines that the black background portion is not the second-direction line segment 4b.

If the processing device 5 determines in step S27 that the black background portion is not the second-direction line segment 4b (step S27: NO), the processing device 5 displays an error on the display device 24 (step S28), and ends the process.

In contrast, if the processing device 5 determines in step S27 that the black background portion is the second-direction line segment 4b (step S27: YES), it finally recognizes the second register mark 4B constituted by the first-direction line segment 4a and the second-direction line segment 4b (step S29).

After detecting the second register mark 4B in step S29, the processing device 5 moves the photosensor 16 via the driving control unit 22 while scanning it on a search path from the second register mark 4B to the third register mark 4C. The process then shifts to step S31.

In step S31, the processing device 5 repetitively executes the above-described processes of steps S22 to S29 on the first-direction line segment 4a and second-direction line segment 4b constituting the third register mark 4C, thereby detecting the third register mark 4C. After detecting the third register mark 4C, the process shifts to the next step S32.

In step S32, as in step S31, the processing device 5 repetitively executes the above-described processes of steps S22 to S29 on the first-direction line segment 4a and second-direction line segment 4b constituting the fourth register mark 4D, thereby detecting the fourth register mark 4D. Thereafter, the process ends.

As described above, the processing device 5 applies, to a sensor output, a filter f having a filter width corresponding to the line width h of the first register mark 4A that has actually been measured by the register mark detection unit 27. By using the thresholds VTX and VTY stored in advance in the storage unit 27e, the processing device 5 determines whether the black background portion of the cutting target medium 2 is the first-direction line segment 4a or second-direction line segment 4b constituting each of the second to fourth register marks 4B to 4D. While excluding dust, a wrinkle of the cutting target medium 2, or the like on the search path SCR, the processing device 5 can accurately detect, as a line segment, only the first-direction line segment 4a or second-direction line segment 4b constituting the second to fourth register marks 4B to 4D.

<Other Embodiment>

The above-described embodiment has explained a case in which not only the line width h of the first-direction line segment 4a but also the line width h in the second direction is detected. However, the present invention is not limited to this. For example, if a line width h of a first-direction line segment 4a and the line width h of a second-direction line segment 4b coincide with each other, the line width h of the second-direction line segment 4b need not be detected after detecting the line width h of the first-direction line segment 4a.

The above-described embodiment has explained a case in which the line widths h of the first-direction line segment 4a and second-direction line segment 4b constituting the register mark 4 of the cutting target medium 2 are detected, respectively. However, the present invention is not limited to this. For example, the values of the line widths h of the first-direction line segment 4a and second-direction line segment 4b may be held in application data, read out, and used. In this case, neither the line widths h of the first-direction line segment 4a nor second-direction line segment 4b need be detected.

Also, the above-described embodiment has explained a case in which the second-direction line segment 4b is detected after detecting first the first-direction line segment 4a constituting the register mark 4. Reversely, after detecting first the second-direction line segment 4b, the first-direction line segment 4a may be detected.

Further, the above-described embodiment has explained a case in which the processing device 5 of the cutting plotter 1 includes the register mark detection unit 27. However, a register mark detection unit 27 including a filter holding unit 27a, a filter output determination unit 27b, a line segment determination unit 27c, a line width detection unit 27d, and a storage unit 27e need not always be constituted in a cutting plotter 1. For example, the register mark detection unit 27 may be constituted by software by installing a control program from a recording medium or the Internet in a host device 25 connected to the cutting plotter 1.

The above-described embodiment assumes that a register mark is a "black background portion", i.e., a region lower in reflectance than the background color of a cutting target medium. However, a register mark may be a region higher in reflectance than the background color of a cutting target medium.

What is claimed is:

1. A line segment detection apparatus comprising:
   a head that supports a sensor configured to detect light reflected by a surface of a cutting target medium and output a signal corresponding to an amount of the detected light;
   a driving unit configured to move said head in two-dimensional directions relatively to the cutting target medium; and
   a processing unit configured to drive said driving unit and perform arithmetic processing on an output of the sensor, said processing unit including:
      a region detection unit configured to detect a region different in reflectance from surroundings based on a change of a signal output from the sensor when the sensor was moved together with said head in a first direction parallel to the cutting target medium; and
      a determination unit configured to, when said region detection unit detects the region, set a first scan section and a second scan section extending from a point in the region respectively to the positive direction and the negative direction of a second direction which is parallel to the cutting target medium and perpendicular to the first direction, and to determine that the region is a line segment in the event that a value corresponding to the color of the line segment is continuously obtained in at least one of the first scan section and second scan section, based on the signal output from the sensor when the sensor scanned the first scan section and the second scan section while passing the point and moving in the second direction.

2. The apparatus according to claim 1, wherein based on a standard deviation of the signal output from the sensor in the first scan section and the second scan section, said determination unit determines whether the region is a line segment.

3. The apparatus according to claim 1, wherein when a peak of the signal output from the sensor is not larger than an arbitrary upper limit value larger than an average value of the signal and is not smaller than a lower limit value smaller than the average value in the first scan section and the second scan section, said determination unit determines that the region is a line segment.

4. The apparatus according to claim 1, wherein said processing unit further includes a filter holding unit configured to store a filter formed from a rectangular function that takes a predetermined value in a section corresponding to a line width of a line segment to be detected, and said region detection unit applies the filter to the signal output from the sensor when the sensor was moved in the first direction, and when an output of the filter exceeds a predetermined threshold, detects the region different in reflectance from the surroundings.

5. The apparatus according to claim 4, wherein said processing unit further includes:
   a line width detection unit configured to, when said determination unit determines that the region is a line segment, detect the line width of the line segment based on the output of the sensor obtained when the sensor crossed the line segment in the first direction; and
   a filter constituting unit configured to constitute a filter by the rectangular function that takes a predetermined value in the section corresponding to the line width, and store the filter in said filter holding unit.

6. A non-transitory computer-readable recording medium recording a control program for a cutting plotter including:
   a head that supports a sensor configured to detect light reflected by a surface of a cutting target medium and output a signal corresponding to an amount of the detected light;
   a driving unit configured to move the head in two-dimensional directions relatively to the cutting target medium; and
   a processing unit configured to control to drive the driving unit and perform arithmetic processing on an output of the sensor, the control program causing a computer constituting the processing unit to execute:
      the detection step of detecting a region different in reflectance from surroundings based on a change of a signal output from the sensor when the sensor was moved together with the head in a first direction parallel to the cutting target medium; and
      the determination step of, when the region is detected in the detection step, setting a first scan section and a second scan section extending from a point in the region respectively to the positive direction and the negative direction of a second direction which is parallel to the cutting target medium and perpendicular to the first direction, and determining that the region is a line segment in the event that a value corresponding to the color of the line segment is continuously obtained in at least one of the first scan section and second scan section, based on the signal output from the sensor when the sensor scanned the first scan section and the second scan section while passing the point and moving in the second direction.

* * * * *